United States Patent [19]

Inoue et al.

[11] Patent Number: 4,634,768

[45] Date of Patent: Jan. 6, 1987

[54] HALO-CONTAINING 3-METHYLFLAVONE-8-CARBOXYLIC ACID DERIVATIVES

[75] Inventors: Hiroshige Inoue, Osaka; Kenichi Fukushima, Arita; Ikuzo Nishiguchi, Hirakata, all of Japan

[73] Assignees: Yamamoto Chemical Industrial Co., Ltd., Wakayama; Osaka Municipal Government, Osaka, both of Japan

[21] Appl. No.: 719,025

[22] Filed: Apr. 4, 1985

Related U.S. Application Data

[63] Continuation of Ser. No. 538,009, Sep. 30, 1983, abandoned.

[30] Foreign Application Priority Data

Sep. 30, 1982 [JP] Japan .................................. 57-171303

[51] Int. Cl.$^4$ .................. C07D 309/32; C07D 405/12; C07D 413/12
[52] U.S. Cl. .................................... 544/151; 544/376; 546/196; 548/525; 549/403
[58] Field of Search ................. 544/151, 376; 546/196; 548/525; 549/403

[56] References Cited

U.S. PATENT DOCUMENTS 2,921,070 1/1960 da Re .................................. 549/403
3,429,896 2/1969 Bossert et al. ...................... 549/403
4,115,567 9/1978 Doria et al. .......................... 549/403

FOREIGN PATENT DOCUMENTS 2051269 2/1972 Fed. Rep. of Germany .
1343118 1/1974 United Kingdom .

OTHER PUBLICATIONS

Pendse et al., Chemical Abstracts, vol. 51, 5061–5062 (1957).

Takahashi et al., J. Pharm. Soc. Japan, vol. 74, pp. 48–51 (1954).
Takahashi et al., Chemical Abstracts, vol. 49, 1623.
Organic Syntheses, pp. 543–545.

Primary Examiner—Robert W. Ramsuer
Attorney, Agent, or Firm—Armstrong, Nikaido, Marmelstein & Kubovcik

[57] ABSTRACT

This invention relates to derivatives of 3-methylflavone-8-carboxylic acid represented by the formula (1)

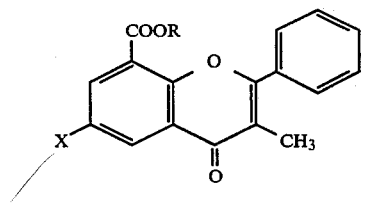

wherein R represents a hydrogen atom, a lower alkyl group or a group

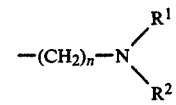

(wherein $R^1$ and $R^2$ represent a lower alkyl group or $R^1$ and $R^2$, when taken together with the nitrogen atom to which they are attached, may form a heterocyclic ring with or without an intervening hetero atom, and n is an integer of 1 to 4), and X represents a halogen atom, which are useful as intermediates.

This invention also relates to processes for preparing the same.

10 Claims, No Drawings

HALO-CONTAINING 3-METHYLFLAVONE-8-CARBOXYLIC ACID DERIVATIVES

This application is a continuation of application Ser. No. 538,009, filed Sept. 30, 1983, now abandoned.

This invention relates to novel derivatives of 3-methylflavone-8-carboxylic acid represented by the formula (1) given below and to processes for preparing the same. The invention also concerns with novel processes for preparing derivatives of 3-methylflavone-8-carboxylic acid represented by the formula (6) shown hereinafter.

The 3-methylflavone-8-carboxylic acid derivatives of the present invention are novel compounds undisclosed in literature and represented by the formula (1)

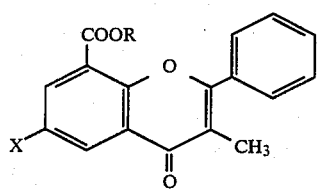
(1)

(wherein R represents a hydrogen atom, a lower alkyl group or a group

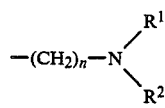

wherein $R^1$ and $R^2$ represent a lower alkyl group or $R^1$ and $R^2$, when taken together with the nitrogen atom to which they are attached, may form a heterocyclic ring with or without an intervening hetero atom, and n is an integer of 1 to 4.), and X represents a halogen atom.

The compounds of this invention represented by the formula (1) are useful as intermediates for synthesizing derivatives of 3-methylflavone-8-carboxylic acid which have pharmacodynamic actions as described below and which are represented by the formula (6)

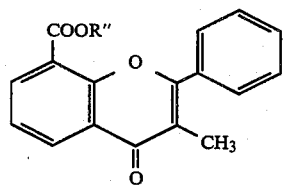
(6)

wherein R" represents a group

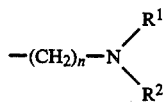

(wherein $R^1$ and $R^2$ are as defined above). The compounds of the formula (6) have an activity of coronary vasodilation and another activity of increasing the coronary blood flow. With these activities, the compounds find applications in treating angina pectoris and in preventing the paroxysm of myocardial infarction and are also usable as a therapeutic agent for inhibiting the increase in a capacity of the bladder, as a remedial agent for treating the pollakisuria anosognosia or as a diuretic having an activity of relaxation for convulsion of smooth muscle of the low urinary tract.

Processes for preparing the compounds of the formula (6) are known, as disclosed, for example, in U.S. Pat. No. 2,921,070 and in Japanese Examined Patent Publication No. 7953/1966. However, these conventional processes have drawbacks as stated below, hence commercially inappropriate. The process described in the U.S. patent attempts to successively produce compounds (II), (III) and (IV) and eventually a compound (V) [which corresponds with the compound of the formula (6)], as shown below in the following reaction equations.

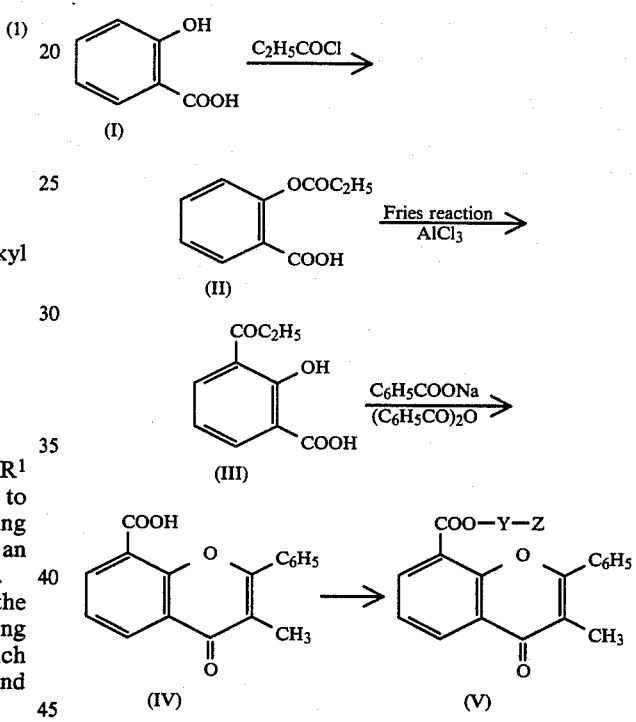

In the foregoing reaction equations, Y represents a divalent, straight alkylene chain having from 2 to 3 carbon atoms and Z represents dimethylamino, diethylamino, di-n-propylamino, diisopropylamino, piperidino or morpholino.

According to the process shown above, however, Fries reaction is carried out to prepare the compound (III) from the compound (II), resulting in the production of the compound (III) in an extremely small amount and the isomer of the compound (III), 2-hydroxy-5-propionylbenzoic acid, in a markedly large amount. This leads to the preparation of the compound (V) in trace amount such that the production of the compound (V) can be barely detected. The manufacture of 2-hydroxy-5-propionylbenzoic acid in large amounts by subjecting the compound (II) to Fries reaction is disclosed, for example, in German Patent Specification No. 2,059,269 and in British Patent Specification No. 1,343,118.

The process stated in Japanese Examined Patent No. 7953/1966 employs 3-allyl-2-hydroxypropiophenone (VI) as the starting material, attempting to prepare compounds (VII) and (IV) and finally the compound (V), as shown in the following reaction equations.

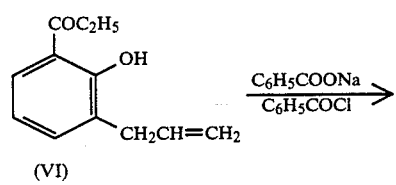

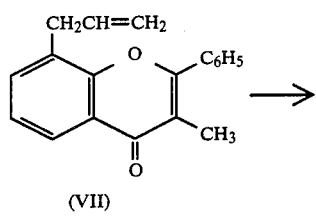

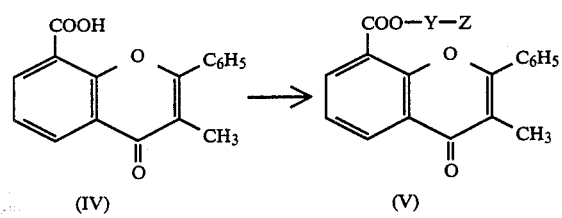

In the foregoing reaction equations, Y and Z are as defined above.

The 3-allyl-2-hydroxypropiophenone (VI) to be used as the starting material in the process is not easily available, because as apparent from the following reaction equations [Org. Synth. coll., 2,543 and Journal of the Pharmaceutical Society of Japan, 74, 48 (1954)], it is difficult to prepare the compound (VI) efficiently from propiophenone (VIII) although the compound (VIII) is readily available.

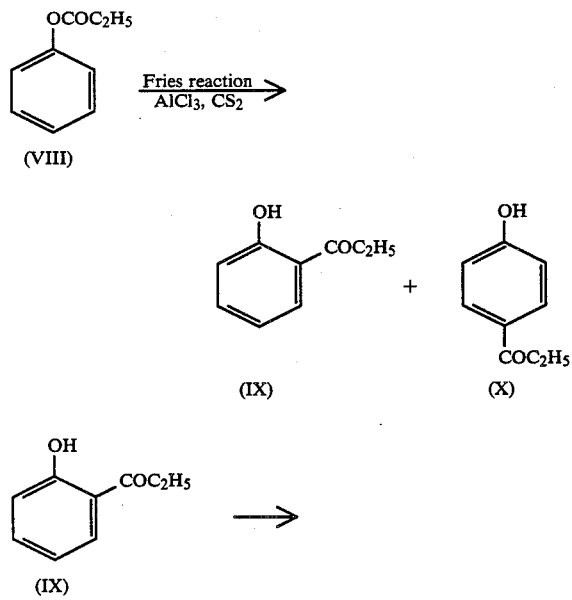

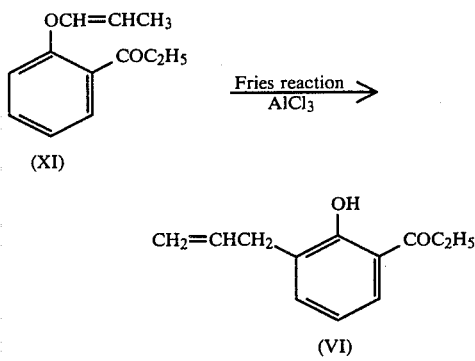

In the above-mentioned process, the compound (VIII) undergoes Fries reaction which produces, in addition to the compound (IX), the compound (X) as a by-product in a larger amount which is difficult to separate from the compound (IX). The production of this by-product involves a cumbersome separating procedure and results in the preparation of the compound (VI) with reduced purity in a lower yield. In short, the process disclosed in Japanese Examined Patent Publication No. 7953/1966 gives the compound (V) in a yield as low as 4 to 5% based on the readily available compound (VIII).

An object of the present invention is to provide the novel derivatives of 3-methylflavone-8-carboxylic acid of the formula (1) which are useful as intermediates for synthesizing derivatives of 3-methylflavone-8-carboxylic acid of the formula (6).

Another object of the invention is to provide processes for preparing the derivatives of 3-methylflavone-8-carboxylic acid of the formula (1).

A further object of the invention is to provide processes for preparing the derivatives of 3-methylflavone-8-carboxylic acid of the formula (6) in a commercially advantageous manner.

Other objects and other features of the invention will become apparent from the following description.

Examples of lower alkyl groups represented by R in the formula (1) are methyl, ethyl, n-propyl, isopropyl, n-butyl and like alkyl groups having 1 to 4 carbon atoms. Examples of the groups

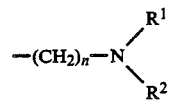

represented by R are dimethylaminomethyl, dimethylaminoethyl, diethylaminopropyl, diethylaminobutyl, di-n-propylaminomethyl, di-n-butylaminoethyl, morpholinomethyl, morpholinoethyl, piperidinomethyl, piperidinoethyl, piperidinopropyl, piperidinobutyl, 1-piperazinylmethyl, 1-piperazinylethyl, pyrrolidinomethyl, pyrrolidinoethyl, pyrrolidinopropyl, etc. Examples of halogen atoms represented by X are fluorine, chlorine, bromine, iodine, etc.

The derivatives of 3-methylflavone-8-carboxylic acid of the formula (1) can be prepared by various processes. A preferred example of the processes comprises heating a derivative of 3-propionylsalicyclic acid represented by the formula (2).

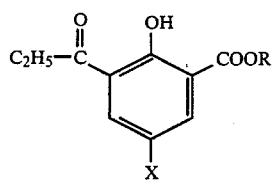

wherein R and X are as defined above, together with an alkali metal salt of benzoic acid and at least one of benzoyl halide and benzoic anhydride in the absence of a solvent.

Examples of benzoyl halides useful in the process are benzoyl chloride, benzoyl bromide, etc. Examples of useful alkali metal salts of benzoic acid are sodium benzoate, potassium benzoate and the like. The amounts of the benzoyl halide or benzoic anhydride and alkali metal salt of benzoic acid are not particularly limited and can be appropriately determined over a wide range. The benzoyl halide and/or benzoic anhydride is used in an amount of usually about 1 to about 8 moles, preferably about 2 to about 5 moles, per mole of the compound of the formula (2). The alkali metal salt of benzoic acid is used in an amount of about 1 to about 8 moles, preferably about 2 to about 5 moles, per mole of the compound of the formula (2). The heating temperature ranges usually from about 150° to about 200° C., preferably from about 180° to about 195° C. The reaction is completed usually in about 5 to about 10 hours.

The compound of the formula (2) to be used as the starting material is a novel one undisclosed in literature and can be prepared for example, by a process comprising subjecting to Friedel-Crafts or Fries reaction a derivative of salicylic acid represented by the formula (3)

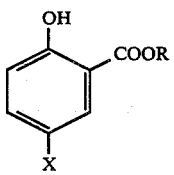

wherein R and X are as defined above and propionyl halide in the presence of a suitable catalyst.

Examples of catalysts useful in the Friedel-Crafts or Fries reaction include a wide variety of catalysts commonly used in this sort of reaction, such as aluminum chloride, ferric chloride, antimony pentachloride, boron trifluoride, zinc chloride, titanium chloride, boron fluoride, sulfuric acid, phosphoric acid, phosphoric anhydride, etc. The amount of such catalysts ranges usually from about 1 to about 4 moles, preferably from about 2 to about 3 moles, per mole of the compound of the formula (3). Examples of useful propionyl halides are propionyl chloride, propionyl bromide and the like. The propionyl halide is used in an amount which is not particularly limitative and which can be suitably selected over a wide range. The amount of the halide is in the range of usually about 1 to about 4 moles, preferably about 2 to about 3 moles, per mole of the compound of the formula (3). The reaction is conducted with or without a solvent, preferably in the absence of a solvent. Useful solvents include carbon disulfide, nitrobenzene, chloroform, carbon tetrachloride, etc. The solvent is employed in an amount substantially equal to that of the compound of the formula (3). The reaction is performed at a temperature ranging usually from room temperature to about 200° C., preferably from about 50° to about 100° C. and is completed in about 2 to about 10 hours.

The compound of the formula (3) to be used as the starting material in the foregoing reaction can be easily prepared by halogenating a salicylic acid represented by the formula (4)

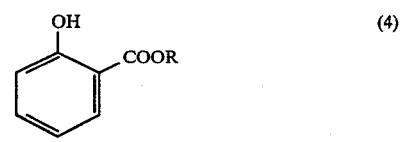

wherein R is as defined above. The halogenation is carried out by reacting the compound of the formula (4) with halogen in a suitable solvent at a temperature in the range of about 0° C. to room temperature for about 1 to about 6 hours. The amounts of the compound of the formula (4) and halogen are not particularly limited and can be determined over a wide range. The latter is used in an amount of usually about 1 to about 2 moles, preferably about 1 to about 1.5 moles, per mole of the former. It is preferred to use as a solvent chloroform which is used usually in an excess amount relative to the compound of the formula (4).

Among the compounds of the formula (2), compounds represented by the formula (2a)

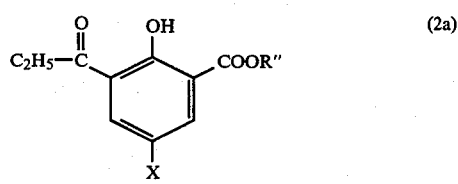

wherein R" represents a group

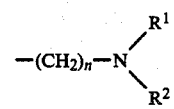

(wherein $R^1$, $R^2$ and n are as defined above) and X is as defined above can be prepared by reacting a derivative of 3-propionylsalicylic acid represented by the formula (2b)

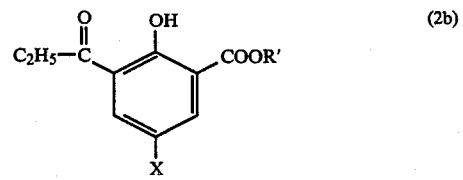

wherein R' represents a hydrogen atom or a lower alkyl group and X is as defined above with an amine represented by the formula (5)

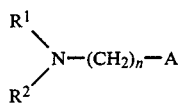

(5)

wherein A represents a halogen atom or a hydroxyl group, and $R^1$, $R^2$ and n are as defined above.

The reaction between the compound of the formula (2b) and the compound of the formula (5) is conducted in the presence of an alkali metal with or without a suitable solvent. Examples of useful solvents are chloroform, carbon tetrachloride and like hydrocarbon halogenides, benzene, toluene, xylene and like aromatic hydrocarbons, etc. The amounts of the compounds of the formulae (2b) and (5) are not particularly limited and can be determined over a wide range. The latter is used in an amount of usually about 1 to about 5 moles, preferably about 1.2 to about 2 moles, per mole of the former. Examples of useful alkali metals are sodium, potassium, etc. The amount of the alkali metal is usually about 0.05 to about 0.5 mole, preferably about 0.1 to about 0.3 mole, per mole of the compound of the formula (2b). The reaction is carried out usually at a temperature of usually about 0° to about 100° C., preferably about 20° to about 80° C., for about 3 to about 5 hours.

Among the compounds of the formula (1), compounds represented by the formula (1a)

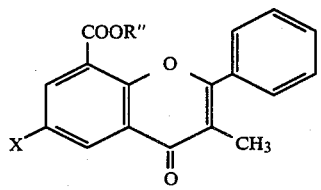

(1a)

wherein R" and X are as defined above can be prepared by reacting a compound represented by the formula (1b)

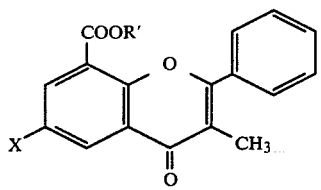

(1b)

wherein R' and X are as defined above with the amine of the formula (5).

The reaction between the compound of the formula (1b) and the amine of the formula (5) can be effected under the same conditions as those which can be employed in the reaction between the compound of the formula (2b) and the amine of the formula (5).

The contemplated compound obtained by each of the foregoing reactions can be separated from the reaction mixture and purified by a conventional method such as distillation, recrystallization, etc.

In any of the above-mentioned processes of the present invention, the reaction procedure is simple; a readily available compound is used as the starting material and the reaction quantitatively proceeds so that the contemplated compound of the formula (6) can be prepared with high purity of over 99.99% in a high yield of over 55% based on the compound of the formula (4).

The compounds of the present invention having the formula (1) are useful as intermediates for synthesizing the derivatives of 3-methylflavone-8-carboxylic acid of the formula (6), as shown in reaction equations given below, which derivatives are usable as therapeutic agents for inhibiting the increase in a capacity of the bladder, mitigating the irritability of the bladder and treating the pollakisuria-residual anosognosia.

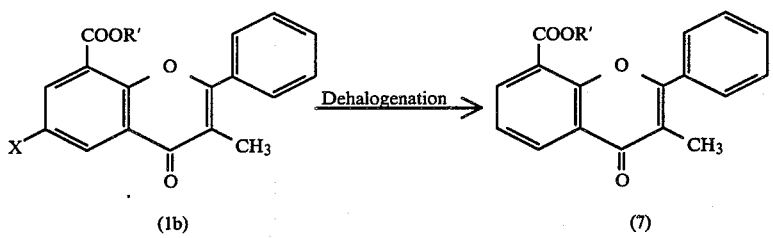

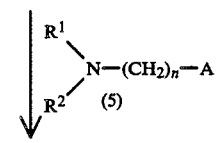

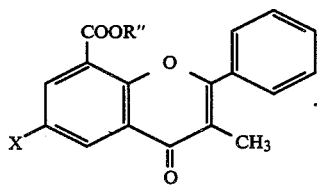

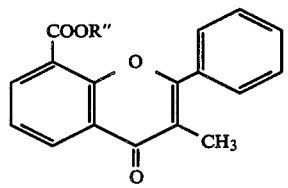

In the foregoing reaction equations, R', R", X, $R^1$, $R^2$, n and A are as defined above.

Examples of catalysts which can be used in dehalogenating the compound of the formula (1a) and the compound (1b) include a wide variety of catalysts heretofore known, such as palladium-carbon, palladium-asbestos, palladium-magnesium sulfate, Raney nickel, platinum black, etc. The amount of the catalyst is usually about 1 to about 10 wt.%, preferably about 3 to about 5 wt.%, based on the compound of the formula (1a) or (1b). The dehalogenation is conducted in a suitable solvent such as methanol, ethanol, n-propanol, isopropanol, n-butanol, isobutanol or like lower aliphatic alcohol, ethyl acetate, butyl acetate, or like acetates, etc. It is preferred to incorporate in the reaction system sodium acetate, sodium propionate, sodium tartrate, sodium citrate or like alkali metal of fatty acid in order to collect the hydrogen chloride produced. The amount of the alkali metal of fatty acid is usually about 0.5 to about 2.5 moles per mole of the compound of the formula (1a) or (1b). The reaction proceeds at a temperature of usually about 10° to about 100° C., preferably about 40° to about 80° C. and is completed usually in about 3 to about 10 hours.

The reaction between the compound of the formula (7) and the amine of the formula (5) is performed under the same conditions as those which are employed in the reaction between the compound of the formula (2a) and the amine of the formula (5).

To clarify the features of the present invention, given below are examples and reference examples in which preparation examples of compounds of the formula (2) are shown.

REFERENCE EXAMPLE 1

Synthesis of methyl 5-chlorosalicylate

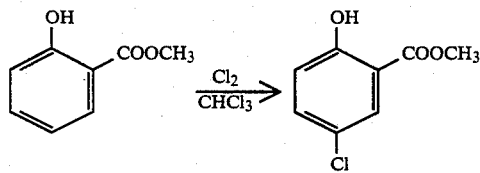

A 85.2 g quantity of chlorine gas was absorbed in a mixture of 152 g (1.0 mole) of methyl salicylate and 500 ml of chloroform at less than 20° C. over a period of 6 hours while the mixture was stirred. The resulting reaction mixture was washed with water and the chloroform was removed. The residue was subjected to fractional distillation at reduced pressure to provide 152 g (81.5%) of a fraction at 117° to 120° C. and 8 mmHg., M.P. 51° C.

REFERENCE EXAMPLE 2

Synthesis of methyl 5-bromosalicylate

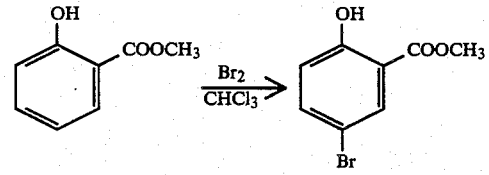

To a mixture of 152 g (1.0 mole) of methyl salicylate and 500 ml of chloroform were added dropwise with stirring a solution of 172 g (1.08 mole) of bromine in 300 ml of chloroform at about 10° C. over a period of 6 hours. After the addition, the mixture was stirred at the same temperature for 1 hour. The reaction mixture was washed with water and then with an aqueous solution of sodium bicarbonate. Removal of the solvent gave 230 g of substantially pure methyl 5-bromosalicylate in 99.6% yield, M.P. 59° to 61.5° C.

REFERENCE EXAMPLE 3

Synthesis of methyl 5-chloro-3-propionylsalicylate

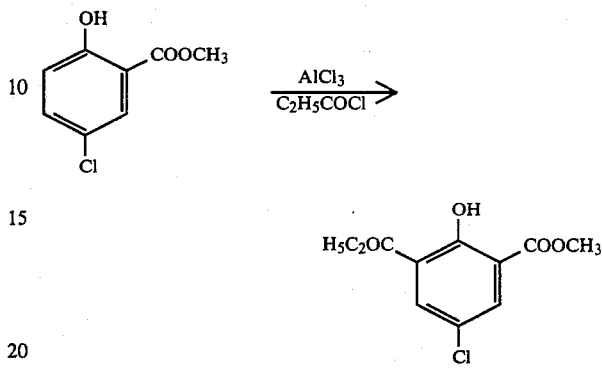

A 80.1 g (0.60 mole) quantity of anhydrous aluminum chloride was added in small amounts with stirring to a mixture of 37.3 g (0.20 mole) of methyl 5-chlorosalicylate and 46.3 g (0.50 mole) of propionyl chloride. The resulting mixture was maintained at room temperature for 1 hour and was heated at 80° C. at which the reaction was continued for 7 hours. After completion of the reaction, the reaction mixture was cooled and water was added thereto in small amounts to decompose the mixture. The resulting mixture was extracted with chloroform. The chloroform was recovered from the chloroform extract and the residue was subjected to distillation at reduced pressure to separate the same into the contemplated product (over 110° C./3 mmHg) and the unreacted material (105° to 110° C./3 mmHg). The fractionation gave 37.5 g of the contemplated product (in a yield of 98.4% based on the consumed amount of the methyl 5-chlorosalicylate) and 8.0 g of the unreacted substance. The purified product was found to have a melting point of 94.0° to 96.8° C.

REFERENCE EXAMPLE 4

Synthesis of methyl 5-bromo-3-propionylsalicylate

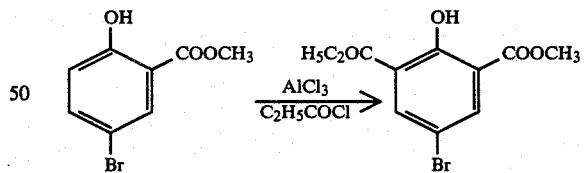

A 80.1 g (0.60 mole) quantity of anhydrous aluminum chloride was added in small amounts with stirring to a mixture of 46.2 g (0.20 mole) of methyl 5-bromosalicylate and 46.3 g (0.50 mole) of propionyl chloride. The resulting mixture was maintained at room temperature and was heated at 80° C. to undergo reaction for 7 hours. After cooling, water was added in small amounts to the reaction mixture to decompose the same. The solution was extracted with chloroform. After removing the solvent, the extract was subjected to distillation at reduced pressure to recover 11.5 g of the unreacted material (at 100° to 118° C. and 3 mmHg). The residue was purified with methanol to give 41.2 g of pale yellow needle-like crystals, methyl 5-bromo-3-propionylsalicylate, M.P. 106.0° to 108.0° C. in a yield of 95.5% based on the consumed amount of the methyl 5-bromosalicylate.

REFERENCE EXAMPLE 5

Synthesis of dimethylaminoethyl 5-chloro-3-propionylsalicylate

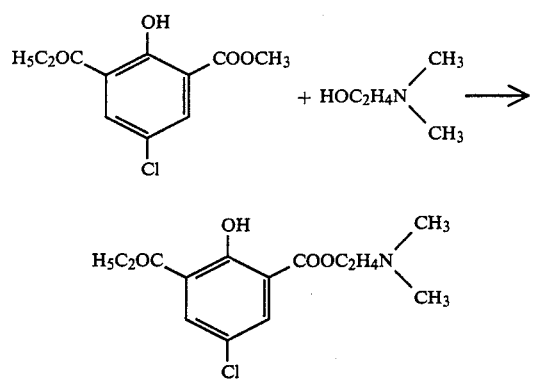

A 24.3 g (0.10 mole) quantity of methyl 5-chloro-3-propionylsalicylate was added to a solution of 0.5 g (0.022 mole) of sodium in 300 ml of dimethylaminoethanol. The mixture was maintained at room temperature for 24 hours and was heated at 90° C. for 2 hours. The reaction mixture was subjected to distillation to remove the excess unreacted dimethylaminoethanol and the methanol produced, and the residue was recrystallized from cyclohexane to obtain 24.2 g (80.7%) of crystals which melt at 48.5° to 51.0° C. The hydrochloride of the product melts at 148.8° to 151.2° C.

REFERENCE EXAMPLE 6

Synthesis of dimethylaminoethyl 5-bromo-3-propionylsalicylate

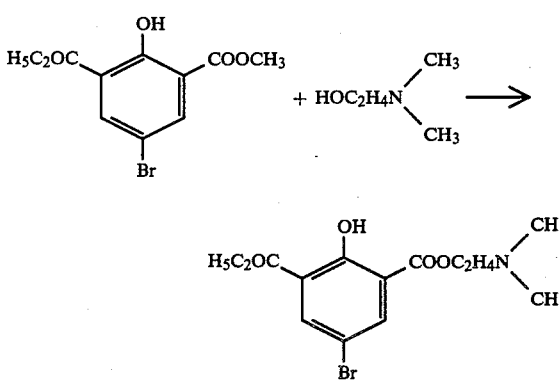

The same procedure as in Reference Example 5 was repeated with the exception of using 28.7 g (0.10 mole) of methyl 5-bromo-3-propionylsalicylate in place of methyl 5-chloro-3-propionylsalicylate, affording 28.0 g (81.4%) of crystals. The hydrochloride of the product melts at 106.6° to 108.0° C.

REFERENCE EXAMPLE 7

Synthesis of morpholinoethyl 5-chloro-3-propionylsalicylate

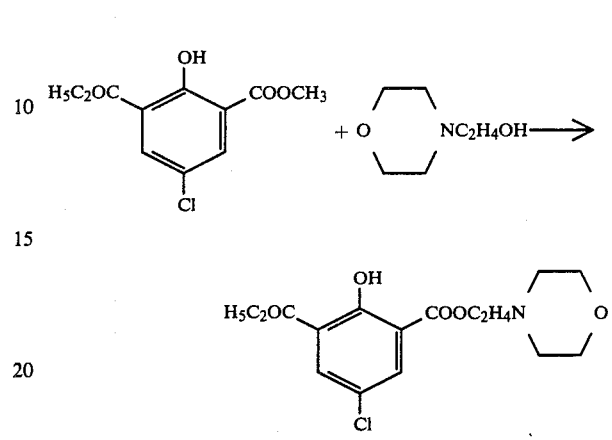

A 24.3 g (0.10 mole) quantity of methyl 5-chloro-3-propionylsalicylate was added to a solution of 0.5 g (0.022 mole) of sodium in 300 ml of morpholinoethanol. The mixture was maintained at room temperature for 24 hours and was heated at 2 hours at 90° C. The reaction mixture was subjected to distillation at reduced pressure to remove the excess unreacted morpholinoethanol and the methanol produced, and the residue was recrystallized from cyclohexane to obtain 38.0 g (88.8%) of crystals which melt at 144.0° to 146.3° C.

REFERENCE EXAMPLE 8

Synthesis of morpholinoethyl 5-bromo-3-propionylsalicylate

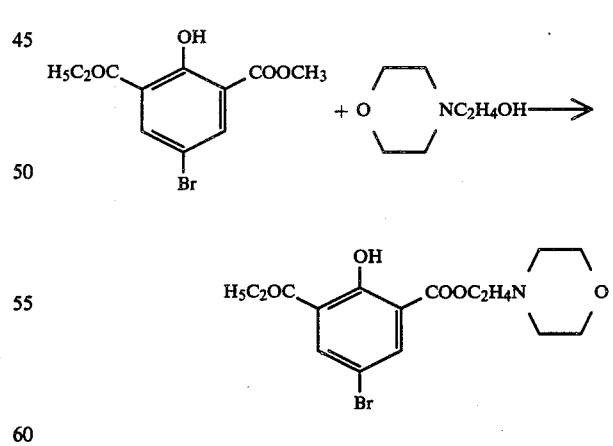

The procedure of Reference Example 7 was repeated with the exception of using 28.7 g (0.10 mole) of methyl 5-bromo-3-propionylsalicylate in place of methyl 5-chloro-3-propionylsalicylate, giving 33.0 g (85.5%) of crystals. The hydrochloride of the product melts at 218.2° to 219.6° C.

REFERENCE EXAMPLE 9

Synthesis of β-piperidinoethyl 5-chloro-3-propionylsalicylate

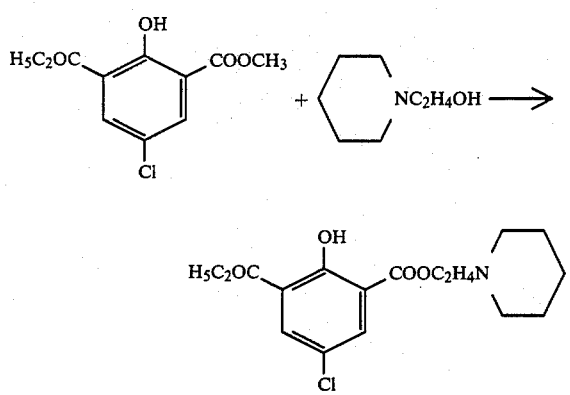

A 24.3 g (0.10 mole) quantity of methyl 5-chloro-3-propionylsalicylate was added to a solution of 0.20 g (0.013 mole) of sodium in 300 ml of piperidinoethanol. The mixture was maintained at room temperature for 24 hours and was heated at 90° C. for 2 hours. The reaction mixture was subjected to distillation at reduced pressure to remove the excess unreacted piperidinoethanol and the methanol produced. The residue was dissolved in dilute hydrochloric acid for purification and was neutralized with sodium carbonate. The separated crystals were collected, washed with water and dried, giving 31.5 g of the contemplated product in a 92.8% yield. The hydrochloride of the product was found to have a melting point of 165.6° to 168° C.

REFERENCE EXAMPLE 10

Synthesis of β-piperidinoethyl 5-bromo-3-propionylsalicylate

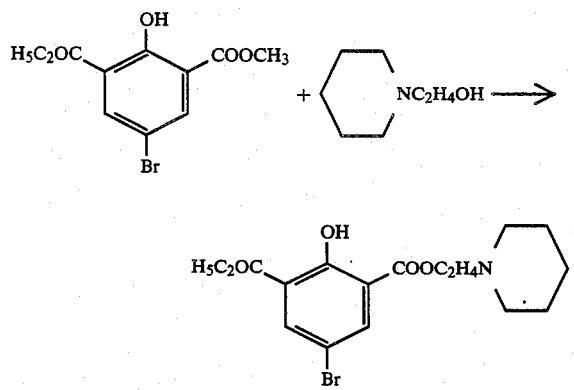

The procedure of Reference Example 9 was repeated with the exception of using 28.7 g (0.10 mole) of methyl 5-bromo-3-propionylsalicylate in place of methyl 5-chloro-3-propionylsalicylate, affording 34.5 g (89.8%) of crystals. The hydrochloride of the product melts at 156.0° to 158.2° C.

EXAMPLE 1

(a) Synthesis of 6-chloro-3-methylflavone-8-carboxylic acid

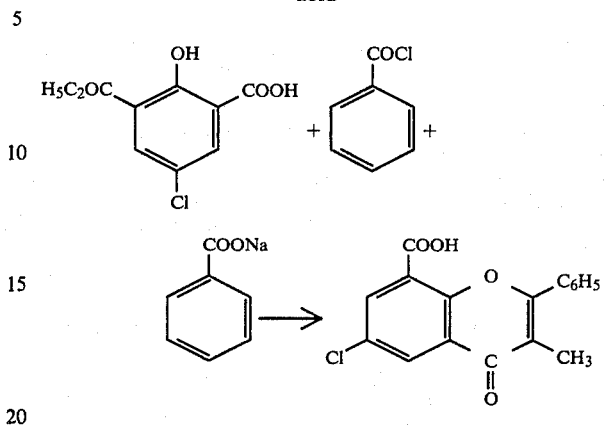

A 47.5 g (0.33 mole) quantity of sodium benzoate was added with stirring to a mixture of 22.9 g (0.10 mole) of 5-chloro-3-propionylsalicylic acid and 42.1 g (0.30 mole) of benzoyl chloride. The reaction mixture was heated at 180° to 190° C. in an oil bath for 8 hours and was cooled. Thereto was added a 5% aqueous solution of sodium carbonate to dissolve the reaction mixture therein. The insolubles were filtered off. The solution was acidified with dilute hydrochloric acid and the separated white crystals were filtered off. The crystals were washed with an aqueous solution of alcohol and dried to obtain 28.6 g (90.9%) of white powder which had a melting point of 309° to 312° C. (sublimation). The compound thus obtained was subjected to chemical analysis with the results shown in Table 1 given below.

(b) Synthesis of 6-chloro-3-methylflavone-8-carboxylic acid

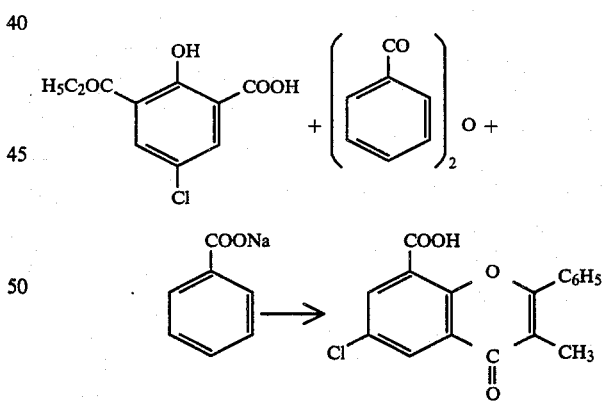

There were mixed together 22.9 g (0.10 mole) of 5-chloro-3-propionylsalicylic acid, 21.6 g (0.15 mole) of sodium benzoate and 48.5 g (0.215 mole) of benzoic anhydride. The mixture was heated at 180° to 190° C. for 6 hours. After cooling, a 5% aqueous solution of sodium carbonate was added to the mixture to dissolve the same therein. The insolubles were filtered off and were acidified with dilute hydrochloric acid and the separated crystals were collected, washed with alcohol and dried to provide 27.5 g (87.6%) of white powder which melts at 309.0° to 312.0° C. The compound thus obtained was chemically analyzed with the results identical with those of the compound given above in (a).

EXAMPLE 2

(a) Synthesis of dimethylaminoethyl 6-chloro-3-methylflavone-8-carboxylate

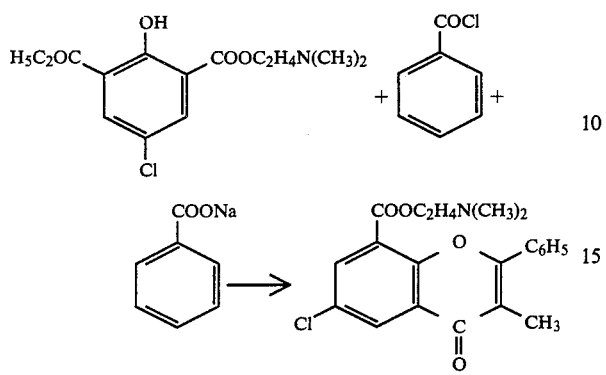

A 47.5 g (0.33 mole) quantity of sodium benzoate was added to a mixture of 30 g (0.10 mole) of dimethylaminoethyl 5-chloro-3-propionylsalicylate and 42.1 g (0.30 mole) of benzoyl chloride. The resulting mixture was reacted in an oil bath at a temperature of 180° to 190° C. for 8 hours. After cooling, dilute hydrochloric acid was added thereto to dissolve the reaction mixture therein and the insolubles were removed. The residue was neutralized with soda ash and the separated solids were extracted with chloroform. The solvent was distilled off to provide 34.5 g (92.8%) of an oily product (which was gradually crystallized).

The oily product was recrystallized from cyclohexane to provide 33.0 g (88.7%) of white powdery crystals which melt at 56.5° to 58.5° C. The compound was chemically analyzed with the results indicated in Table 1 given below. The hydrochloride of the compound had a melting point of 192.7° to 193.4° C.

(b) Synthesis of dimethylaminoethyl 6-chloro-3-methylflavone-8-carboxylate

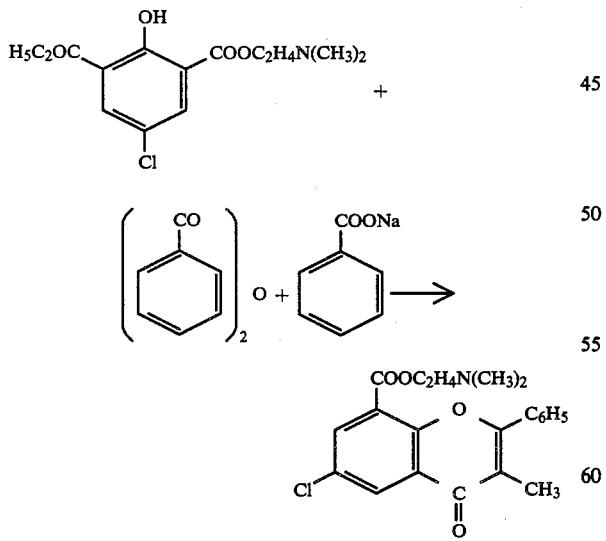

A 48.5 g (0.215 mole) quantity of benzoic anhydride was added to a mixture of 30 g (0.10 mole) of dimethylaminoethyl 5-chloro-3-propionylsalicylate and 21.6 g (0.15 mole) of sodium benzoate. The resulting mixture was reacted in an oil bath at 180° to 190° C. for 6 hours. After cooling, dilute hydrochloric acid was added to dissolve the reaction mixture therein and the insolubles were removed. The residue was neutralized with soda ash and the separated solids were extracted with chloroform. The solvent was distilled off and the residue was recrystallized from cyclohexane to obtain 33.1 g (85.8%) of white needle-like crystals, M.P. 56.5° to 58.5° C. When the product and the compound obtained above in (a) were melted together, the melting point was not lower than that of each compound. Thus these two compounds proved identical.

EXAMPLE 3

Synthesis of morpholinoethyl 6-chloro-3-methylflavone-8-carboxylate

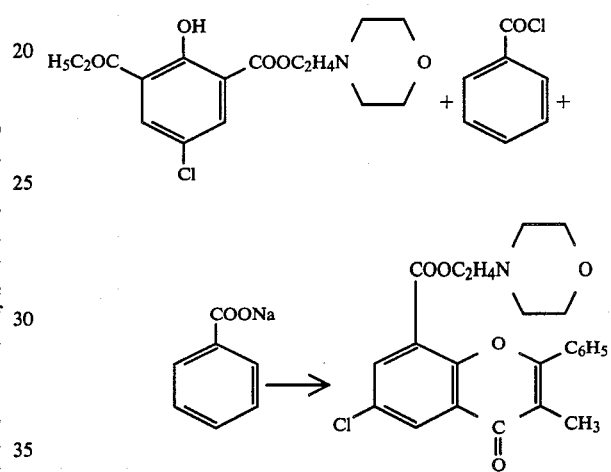

A 23.7 g (0.165 mole) quantity of sodium benzoate was added to a mixture of 17.1 g (0.05 mole) of morpholinoethyl 5-chloro-3-propionylsalicylate and 21.1 g (0.15 mole) of benzoyl chloride. The mixture was heated at 185° to 195° C. in an oil bath for 8 hours. After cooling, a 10% aqueous solution of hydrochloric acid was added to dissolve the reaction mixture therein and the insolubles were removed. The cooled residue was neutralized with soda ash and the separated solids were filtered off and dried to obtain 19.6 g (91.6%) of the contemplated product which melts at 68.0° to 73° C. The product was recrystallized from cyclohexane to give a compound melting at 73.3° to 75.5° C.

The compound thus obtained was chemically analyzed with the results shown in Table 1 below. The hydrochloride of the product was found to have a melting point of 208.4° to 211.5° C.

EXAMPLE 4

Synthesis of methyl 6-chloro-3-methylflavone-8-carboxylate

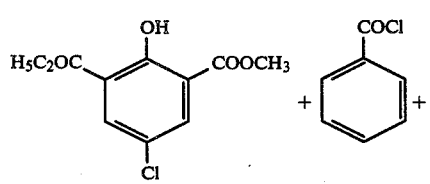

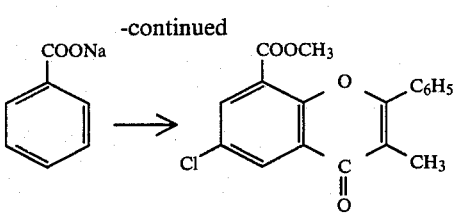

A 23.8 g (0.165 mole) quantity of sodium benzoate was added with stirring to a mixture of 12.1 g (0.05 mole) of methyl 5-chloro-3-propionylsalicylate and 21.1 g (0.15 mole) of benzoyl chloride. The resulting mixture was heated at 180° to 190° C. in an oil bath for 8 hours to undergo reaction. After cooling, 100 ml of a 5% aqueous solution of sodium carbonate was added to the reaction mixture and the admixture was stirred. The solids formed were recrystallized from alcohol, giving 14.8 g (90.1%) of white crystal, which was repeatedly recrystallized from alcohol to obtain a compound having a melting point of 171.5° to 173.0° C. The compound was chemically analyzed with the results shown in Table 1 given below.

EXAMPLE 5

Synthesis of ethyl 6-chloro-3-methylflavone-8-carboxylate

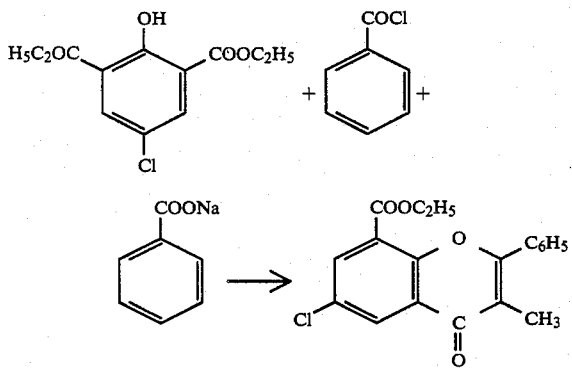

A 23.8 g (0.165 mole) quantity of sodium benzoate was added with stirring to a mixture of 12.8 g (0.05 mole) of ethyl 5-chloro-3-propionylsalicylate and 21.1 g (0.15 mole) of benzoyl chloride. The resulting mixture was heated at 180° to 190° C. for 8 hours to undergo reaction. The reaction mixture was cooled and 100 ml of a 5% aqueous solution of sodium carbonate was added. The mixture was stirred to precipitate solids. The solids were recrystallized from alcohol, giving 15.3 g (89.5%) of white crystals, M.P. 127.0° to 128.2° C. Table 1 below shows the results of chemical analysis.

EXAMPLE 6

Synthesis of β-piperidinoethyl 6-chloro-3-methylflavone-8-carboxylate

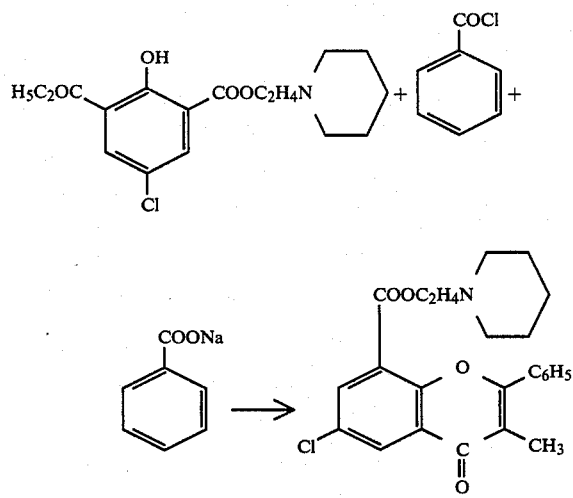

A 14.4 g (0.1 mole) quantity of sodium benzoate was added with stirring to a mixture of 10.2 g (0.03 mole) of β-piperidinoethyl 5-chloro-3-propionylsalicylate and 12.6 g (0.09 mole) of benzoyl chloride. The resulting mixture was heated in an oil bath at 180° to 190° C. for 8 hours to undergo reaction. After cooling, a 5% aqueous solution of sodium carbonate was added to the reaction mixture. The solids formed were purified with alcohol to provide 10.6 g (83.0%) of white crystals which were treated with a hydrochloric acid-alcohol mixture and were recrystallized from alcohol. The hydrochloride of the compound was found to have a melting point of 196.1° to 198.3° C.

The compound was subjected to chemical analysis with the results shown in Table 1 below.

TABLE 1

| Ex. | Solvent | NMR spectrum δ value (ppm) | IR spectrum (cm$^{-1}$) | MASS spectrum (m/e) | Elementary analysis Calcd. | | Found |
|---|---|---|---|---|---|---|---|
| 1 | DMSO—d$_6$ | 8.49 (br. s, 2H), 8.37–8.07 (m, 2H), 8.07–7.77 (m, 3H), 2.21 (s, 3H) | 3350– 3300 1705 1610 | 316,314 (Molecular peak) | C$_{17}$H$_{11}$ClO$_4$ C: 64.88% H: 3.52% Cl: 11.26% | C: H: Cl: | 64.80% 3.50% 11.25% |
| 2 | CDCl$_3$ | 8.35 (d, 1H), 8.16 (d, 1H), 7.82–7.62 (m, 2H), 7.62–7.21 (m, 3H), 4.49 (t, 2H), 2.73 (t, 2H), 2.32 (s, 6H), 2.22 (s, 3H) | 1720 1640 | 373,371 (Molecular peak) | C$_{21}$H$_{20}$ClO$_4$ C: 67.83% H: 5.42% Cl: 9.53% | C: H: Cl: | 67.81% 5.40% 9.51% |
| 3 | CDCl$_3$ | 8.36 (d, 1H), 8.15 (d, 1H), 7.90–7.61 (m, 2H), 7.61–7.34 (m, 3H), 4.47 (t, 2H), 3.64 (t, 4H), 2.70 (t, 2H), 2.45 (t, 2H), 2.21 (s, 3H) | 1720 1640 | 415,413 (Molecular peak) | C$_{23}$H$_{22}$ClO$_5$ C: 66.75% H: 5.36% Cl: 8.57% | C: H: Cl: | 66.74% 5.33% 8.49% |
| 4 | CDCl$_3$ | 8.58–8.50 (m, 1H), 8.38–8.30 (m, 1H), 8.20–7.88 (m, 2H), 7.78–7.62 (m, 3H), 4.02 (s, 3H), 2.27 (s, 3H) | 1720 1640 | 330,328 (Molecular peak) | C$_{18}$H$_{13}$ClO$_4$ C: 65.76% H: 3.99% Cl: 10.78% | C: H: Cl: | 65.72% 3.92% 10.71% |

TABLE 1-continued

| Ex. | NMR spectrum Solvent | δ value (ppm) | IR spectrum (cm⁻¹) | MASS spectrum (m/e) | Elementary analysis | Calcd. | | Found |
|---|---|---|---|---|---|---|---|---|
| 5 | DMSO—$d_6$ | 8.38 (br. s, 2H), 8.20–8.00 (m, 2H), 8.00–7.77 (m, 3H), 4.51 (q, 2H), 2.12 (s, 3H), 1.33 (t, 3H) | 1710 1640 | 344,342 (Molecular peak) | $C_{19}H_{15}ClO_4$ | C: 66.58% H: 4.41% Cl: 10.34% | C: H: Cl: | 66.57% 4.37% 10.33% |
| 6 | DMSO—$d_6$ | 8.51 (d, 1H), 8.30 (d, 1H), 8.06–7.90 (m, 2H), 7.90–7.70 (m, 3H), 4.92–4.76 (m, 2H), 3.73–2.74 (m, 6H), 2.10 (s, 3H), 1.96–1.30 (m, 6H) | 1720 1640 | 414,412 (Molecular peak) | $C_{24}H_{25}Cl_2O_4$ | C: 64.29% H: 5.62% Cl: 15.81% | C: H: Cl: | 64.27% 5.20% 15.77% |

EXAMPLE 7

(a) Synthesis of 6-bromo-3-methylflavone-8-carboxylic acid

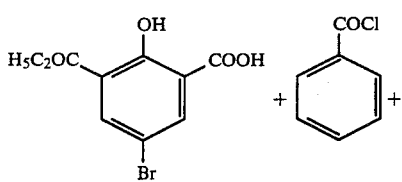

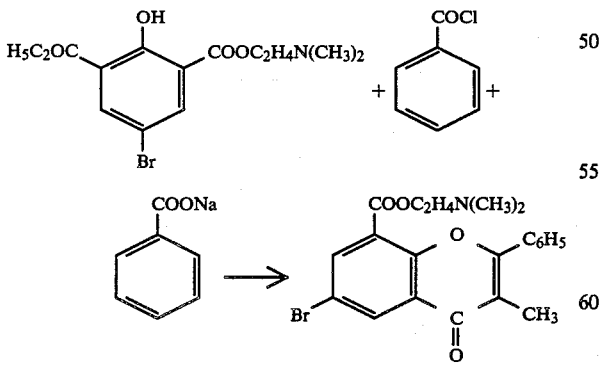

The procedure of Example 1, (a) was repeated with the exception of using 27.3 g (0.10 mole) of 5-bromo-3-propionylsalicylic acid in place of 5-chloro-3-propionylsalicylic acid, giving 32.3 g (90.0%) of powdery crystals, M.P. 287.0° to 289.0° C. Table 2 below shows the results obtained by chemically analyzing this compound.

EXAMPLE 8

Synthesis of dimethylaminoethyl 6-bromo-3-methylflavone-8-carboxylate

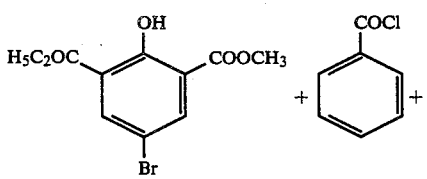

The procedure of Example 2, (a) was followed with the exception of using 34.4 g (0.10 mole) of dimethylaminoethyl 5-bromo-3-propionylsalicylate in place of dimethylaminoethyl 5-chloro-3-propionylsalicylate, giving 38.0 g (88.3%) of crystals. The hydrochloride of the product melts at 192.0° to 195.4° C. Table 2 below shows the results obtained by chemically analyzing this compound.

EXAMPLE 9

Synthesis of morpholinoethyl 6-bromo-3-methylflavone-8-carboxylate

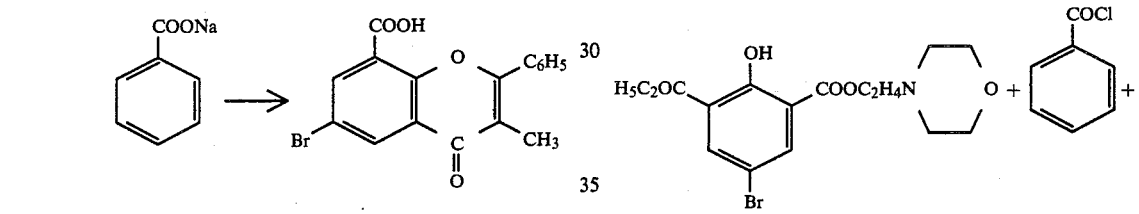

The procedure of Example 3 was repeated with the exception of using 19.3 g (0.05 mole) of morpholinoethyl 5-bromo-3-propionylsalicylate in place of morpholinoethyl 5-chloro-3-propionylsalicylate, giving 21.0 g (89.0%) of crystals. The hydrochloride of the product melts at 205.0° to 208.0° C. Table 2 below shows the results obtained by chemically analyzing this compound.

EXAMPLE 10

(a) Synthesis of methyl 6-bromo-3-methylflavone-8-carboxylate

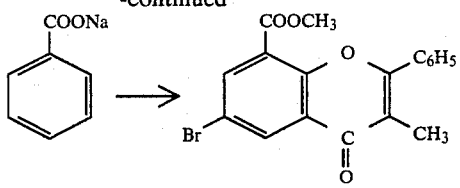

The procedure of Example 4 was repeated with the exception of using 14.3 g (0.05 mole) of methyl 5-bromo-3-propionylsalicylate in place of methyl 5-chloro-3-propionylsalicylate. The resulting product was purified with alcohol to give 15.8 g (84.7%) of white needle-like crystals melting at 171.0° to 175° C. The crystals were recrystallized repeatedly from alcohol, affording a product melting at 174.0° to 175.5° C.

(b) Synthesis of ethyl
6-bromo-3-methylflavone-8-carboxylate

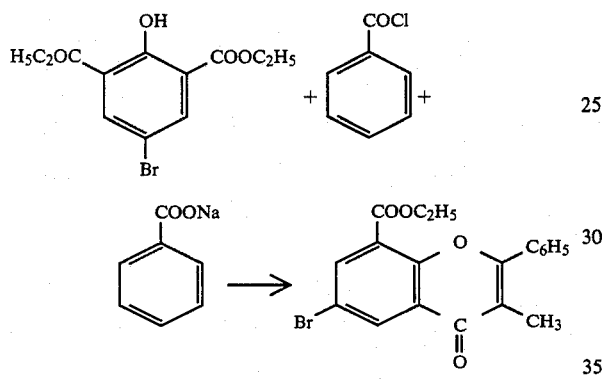

The procedure of Example 5 was repeated with the exception of using 15.0 g (0.05 mole) of ethyl 5-bromo-3-propionylsalicylate in place of ethyl 5-chloro-3-propionylsalicylate. The resulting product was purified with alcohol to give 16.5 g (85.0%) of white needle-like crystals melting at 151.0° to 152.5° C. Table 2 below shows the results obtained by chemically analyzing this compound.

EXAMPLE 11

Synthesis of β-piperidinoethyl
6-bromo-3-methylflavone-8-carboxylate

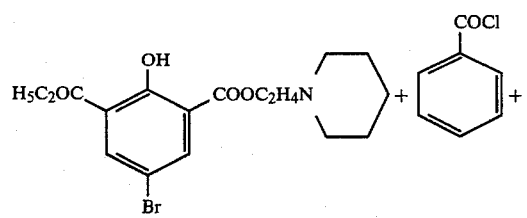

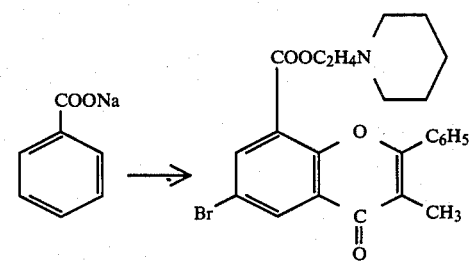

The procedure of Example 6 was repeated with the exception of using 11.5 g (0.03 mole) of β-piperidinoethyl 5-bromo-3-propionylsalicylate in place of β-piperidinoethyl 5-chloro-3-propionylsalicylate, giving 12.0 g (85.1%) of white crystals. The hydrochloride of the product melts at 220.4° to 221.8° C. Table 2 below shows the results obtained by chemically analyzing this compound.

TABLE 2

| Ex. | Solvent | NMR spectrum δ value (ppm) | IR spectrum (cm$^{-1}$) | MASS spectrum (m/e) | Elementary analysis Calcd. | | Found | |
|---|---|---|---|---|---|---|---|---|
| 7 | DMSO-d$_6$ | 13.96 (br. s., 1H), 8.54–8.41 (m, 2H), 8.09–7.92 (m, 2H), 7.86–7.70 (s, 3H), 2.21 (s, 3H) | 3450 1730 1640 | 358,360 (Molecular peak) | C$_{17}$H$_{11}$O$_4$Br C: H: Br: | 56.85% 3.09% 22.24% | C: H: Br: | 56.89% 3.10% 22.21% |
| 8 | DMSO-d$_6$ | 8.98 (d, 1H), 8.70 (d, 1H), 8.35–8.15 (m, 2H), 8.15–7.97 (m, 3H), 5.07–4.85 (m, 2H), 3.87–3.61 (m, 2H), 2.95 (s, 6H), 2.15 (s, 3H) | 1720 1640 | 430,432 (Molecular peak) | C$_{21}$H$_{20}$BrNO$_4$HCl C: H: N: Br: Cl: | 54.04% 4.53% 3.00% 17.12% 7.60% | C: H: N: Br: Cl: | 54.12% 4.54% 2.98% 17.10% 7.54% |
| 9 | DMSO-d$_6$ | 9.01 (d, 1H), 8.79 (d, 1H), 8.40–8.20 (m, 2H), 8.18–8.02 (m, 3H), 5.16–4.96 (m, 2H), 4.30–4.02 (m, 4H), 3.92–3.44 (m, 6H), 2.20 (s, 3H) | 1715 1630 | 472,474 (Molecular peak) | C$_{23}$H$_{22}$BrNO$_5$HCl C: H: N: Br: Cl: | 54.30% 4.56% 2.75% 15.70% 6.97% | C: H: N: Br: Cl: | 54.28% 4.60% 2.72% 15.69% 6.99 |
| 10a | DMSO-d$_6$ | 8.40 (br. s., 2H), 8.06–7.90 (m, 2H), 7.90–7.70 (m, 3H), 3.99 (s, 3H), 2.16 (s, 3H) | 1720 1640 | 372,374 (Molecular peak) | C$_{18}$H$_{13}$O$_4$Br C: H: Br: | 57.93% 3.51% 21.41% | C: H: Br: | 57.88% 3.59% 21.48% |
| 10b | CCl$_4$ | 8.70 (d, 1H), 8.47 (d, 1H), 8.12–7.96 (m, 2H), 7.82–7.68 (m, 3H), 4.32 (q, 2H), 2.24 (s, 3H), 1.42 (t, 3H) | 1710 1630 | 386,388 (Molecular peak) | C$_{19}$H$_{15}$BrO$_4$ C: H: Br: | 58.93% 3.90% 20.63% | C: H: Br: | 58.99% 3.94% 20.59% |
| 11 | DMSO-d$_6$ | 8.92 (d, 1H), 8.71 (d, 1H), 8.35–8.16 (m, 2H), 8.15–7.98 (m, 3H), 5.10–4.88 (m, 2H) | 1740 1640 | 470,472 (Molecular peak) | C$_{24}$H$_{24}$BrNO$_4$HCl C: H: N: | 56.88% 4.97% 2.76% | C: H: N: | 56.83% 4.95% 2.74% |

TABLE 2-continued

| Ex. | Solvent | NMR spectrum δ value (ppm) | IR spectrum (cm$^{-1}$) | MASS spectrum (m/e) | Elementary analysis Calcd. | Found |
|---|---|---|---|---|---|---|
| | | 3.84–2.78 (m, 6H), 2.12 (s, 3H), 2.04–1.58 (m, 6H) | | | Br: 15.76% Cl: 7.00% | Br: 15.82% Cl: 7.06% |

EXAMPLE 12

Synthesis of dimethylaminoethyl 6-chloro-3-methylflavone-8-carboxylate hydrochloride

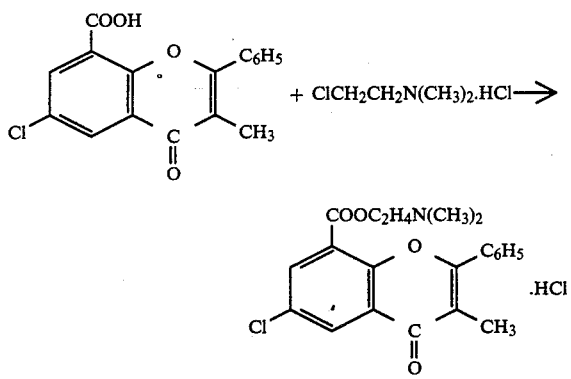

A 100 ml quantity of xylene was added to a mixture of 15.7 g (0.05 mole) of 6-chloro-3-methylflavone-8-carboxylic acid and 7.9 g (0.055 mole) of hydrochloride of N,N-dimethylaminoethylchloride. The resulting mixture was refluxed with heating for 5 hours. After cooling, the crystals precipitated were filtered off, washed with xylene and dried to give 20.2 g (95.7%) of white crystals which melt at 188.5° to 192.5° C. The crystals were recrystallized repeatedly from alcohol to provide 17.8 g (84.3%) of white crystals having a melting point of 192.7° to 193.4° C. Table 1 above shows the results of chemical analysis in respect of this compound. The compound and the dimethylaminoethyl 6-chloro-3-methylflavone-8-carboxylate hydrochloride obtained by the process of Example 2 were melted together and the melting point was not lower than that of the compound obtained in this example.

EXAMPLE 13

Synthesis of morpholinoethyl 6-chloro-3-methylflavone-8-carboxylate

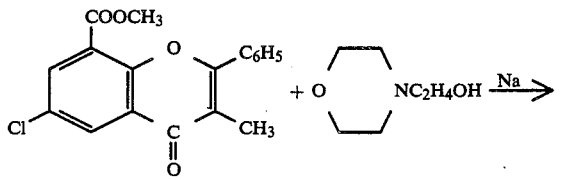

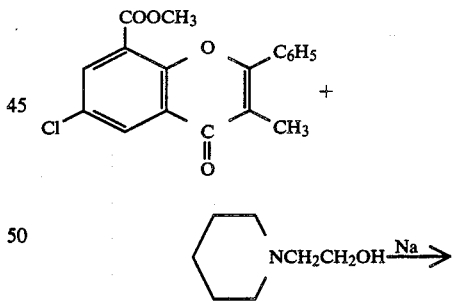

A 32.9 g (0.10 mole) quantity of methyl 6-chloro-3-methylflavone-8-carboxylate was added to a solution of 0.5 g (0.022 mole) of sodium in 300 ml of morpholinoethanol. The mixture was maintained at room temperature for 24 hours and heated at 90° C. for 2 hours. The excess morpholinoethanol and the methanol produced were distilled off the reaction mixture at reduced pressure. The residue was purified with alcohol, giving 40.6 g (94.9%) of white needle-like crystals which melt at 73.3° to 75.5° C. The crystals and the product obtained in Example 3 were melted together and the melting point was not lower than that of each compound. The hydrochloride of the product given in this example had a melting point of 208.4° to 211.5° C.

EXAMPLE 14

Synthesis of β-piperidinoethyl 6-chloro-3-methylflavone-8-carboxylate

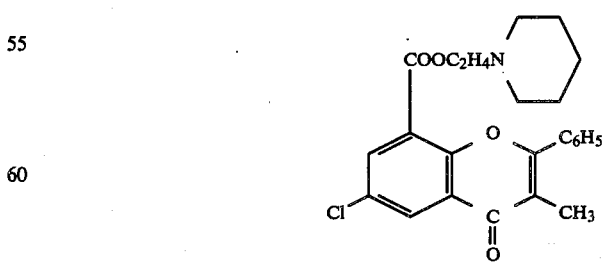

A 32.9 g (0.10 mole) quantity of methyl 6-chloro-3-methylflavone-8-carboxylate was added to a solution of 0.5 g (0.022 mole) of sodium in 300 ml of piperidinoethanol. The mixture was maintained at room temperature for 24 hours and was heated at 90° C. for 2 hours. The excess piperidinoethanol and the methanol produced were removed from the reaction mixture by distillation. The residue was dissolved in dilute hydrochloric acid, purified and neutralized in the usual manner, giving 42.0 g (98.7%) of a product. The product was treated with a hydrochloric acid-alcohol mixture and recrystallized from alcohol to provide β-piperidinoethyl 6-chloro-3-methylflavone-8-carboxylate hydrochloride which was found identical with the compound obtained in Example 6.

EXAMPLE 15

Synthesis of β-piperidinoethyl 6-chloro-3-methylflavone-8-carboxylate hydrochloride

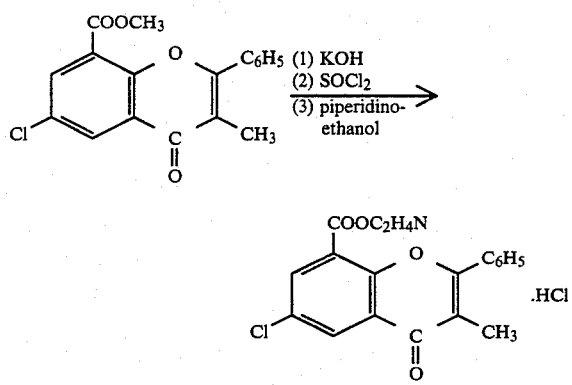

A 32.9 g (0.10 mole) quantity of methyl 6-chloro-3-methylflavone-8-carboxylate was added to 200 ml of a solution of 0.5N—KOH in methanol. The mixture was refluxed with heating for 3 hours and the solvent was removed by distillation. The residue was dissolved in 300 ml of water and the solution was neutralized with dilute hydrochloric acid to provide 30.2 g (96.0%) of white powder which melts at 309° to 312° C. The powder was found identical with the 6-chloro-3-methylflavone-8-carboxylic acid obtained in Example 1, (a) and (b).

A 15.0 g (0.126 mole) quantity of thionyl chloride and 100 ml of anhydrous benzene were added to 15.7 g (0.05 mole) of the 6-chloro-3-methylflavone-8-carboxylic acid. The mixture was refluxed with heating for 5 hours and the benzene and excess thionyl chloride were recovered at reduced pressure to obtain 16.5 g of residual solids, 6-chloro-3-methylflavone-8-carbonyl chloride. To the solids were added 7.0 g (0.054 mole) of piperidinoethanol and 100 ml of anhydrous benzene. The mixture was refluxed with heating for 3 hours to provide white crystals which were filtered off, washed with benzene and dried, giving 22.6 g of a product in a 97.8% yield. The product was recystallized several times from alcohol to afford 20.5 g (88.7%) of white needle-like crystals, which melt at 196.1° to 198.3° C. The product and the hydrochloride of β-piperidinoethyl 6-chloro-3-methylflavone-8-carboxylate hydrochloride obtained in Example 6 were melted together and the melting point was not lower than that of the product prepared in this example. Thus the two compounds were identical.

EXAMPLE 16

Synthesis of dimethylaminoethyl 6-bromo-3-methylflavone-8-carboxylate hydrochloride

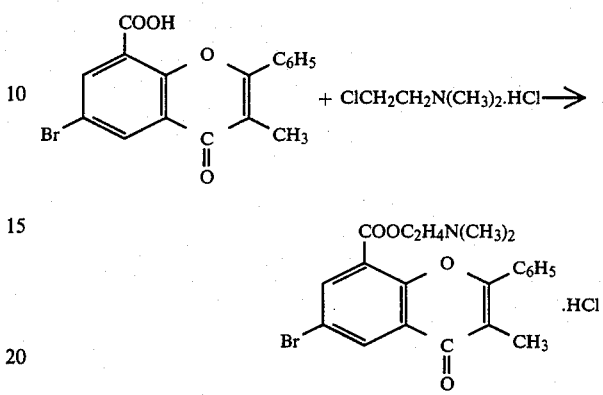

The procedure of Example 12 was repeated with the exception of using 17.9 g (0.05 mole) of 6-bromo-3-methylflavone-8-carboxylic acid in place of 6-chloro-3-methylflavone-8-carboxylic acid, giving 22.0 g (94.3%) of crystals. The crystals were recrystallized from alcohol to obtain 20.0 g (85.7%) of white needle-like crystals melting at 192.0° to 195.4° C. The crystals were found to be identical with the product obtained in Example 8.

EXAMPLE 17

Synthesis of morpholinoethyl 6-chloro-3-methylflavone-8-carboxylate

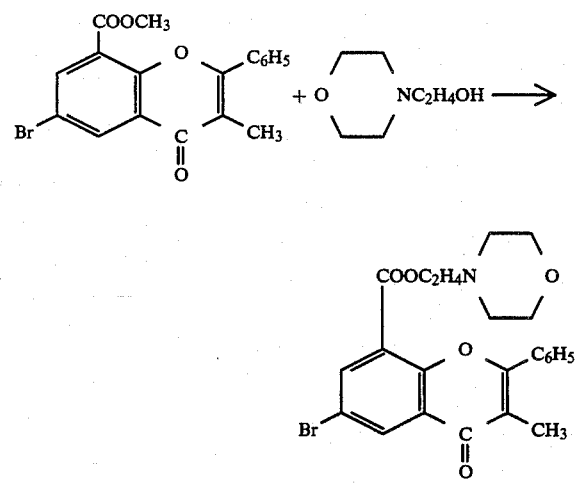

The procedure of Example 13 was repeated with the exception of using 37.3 g (0.10 mole) of methyl 6-bromo-3-methylflavone-8-carboxylate in place of methyl 6-chloro-3-methylflavone-8-carboxylate, giving 44 g (93.2%) of crystals. The hydrochloride of the product melts at 205.0° to 208.0° C. The crystals were found to be identical with the product obtained in Example 9.

EXAMPLE 18

Synthesis of β-piperidinoethyl 6-bromo-3-methylflavone-8-carboxylate

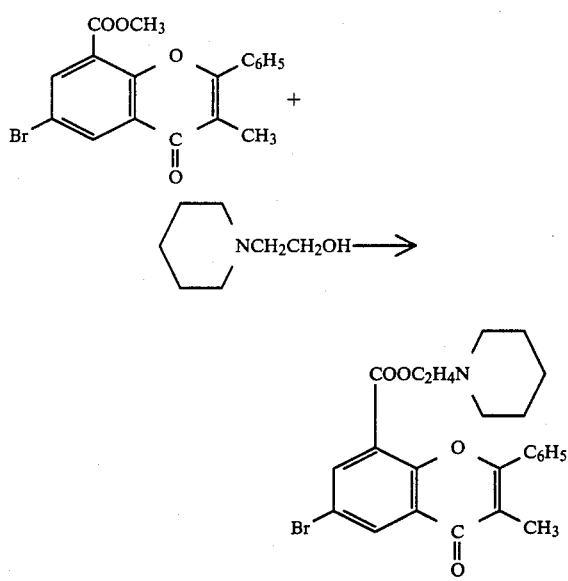

The procedure of Example 14 was repeated with the exception of using 37.3 g (0.10 mole) of methyl 6-bromo-3-methylflavone-8-carboxylate in place of methyl 6-chloro-3-methylflavone-8-carboxylate, giving 44.6 g (94.9%) of a reaction product which was recrystallized from alcohol to give 41.8 g (88.9%) of white crystals, M.P. 220.4° to 222.0° C. The crystals were found to be identical with the product obtained in Example 11.

EXAMPLE 19

Synthesis of β-piperidinoethyl 6-bromo-3-methylflavone-8-carboxylate hydrochloride

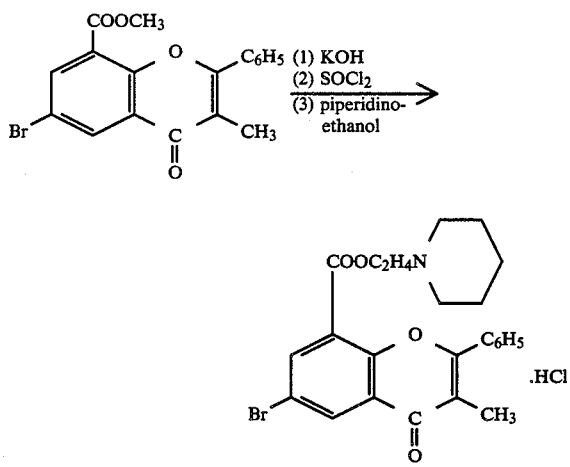

The procedure of Example 15 was repeated with the exception of using 37.3 g (0.10 mole) of methyl 6-bromo-3-methylflavone-8-carboxylate in place of methyl 6-chloro-3-methylflavone-8-carboxylate. The resulting product was recrystallized from alcohol to give 22.0 g (86.8%) of white crystals melting at 220.4° to 221.8° C.

EXAMPLE 20

Synthesis of methyl 3-methylflavone-8-carboxylate

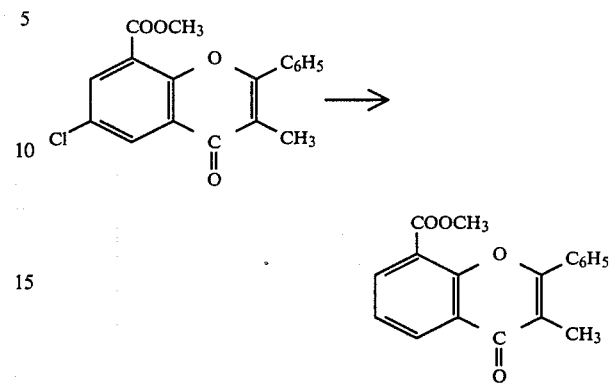

Into a pressure reactor were placed 1.5 g (4.57 m mole) of methyl 6-chloro-3-methylflavone-8-carboxylate, 1.8 g (14.2 m mole) of sodium acetate, 150 ml of isopropanol and 0.075 g of 5% palladium-carbon. After the atmosphere was replaced with hydrogen gas, reaction was conducted at 70° C. under a pressure of 5.0 kg/cm²G for 6 hours. Thereafter the contents were withdrawn from the reactor and were subjected to filtration while being hot to remove the catalyst. The solvent was recovered from the filtrate to provide 1.1 g (82.1%) of white needle-like crystals which melt at 162.2° to 164.8° C. The crystals were recrystallized from alcohol to obtain a product having a melting point of 166.4° to 168.2° C. The product was found identical in melting point with the compound prepared by the conventional method. When the product of this example and the compound prepared by the conventional method were melted together, the melting point was not lower than that of the product of this example.

EXAMPLE 21

Synthesis of dimethylaminoethyl 3-methylflavone-8-carboxylate

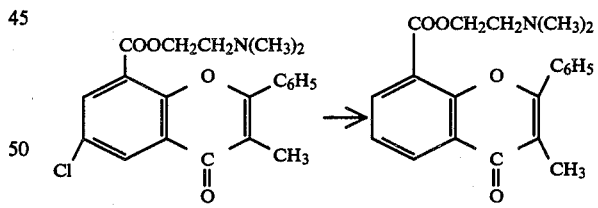

Into a pressure reactor were placed 3.9 g (0.01 mole) of dimethylaminoethyl 6-chloro-3-methylflavone-8-carboxylate, 2.7 g (0.02 mole) of sodium acetate, 150 ml of isopropanol and 0.16 g of 5% palladium-carbon catalyst. After the atmosphere was replaced with hydrogen gas, reaction was conducted at a pressure of 5.0 kg/cm²G at 50° C. for 6 hours. After completion of the reaction, the contents were withdrawn from the reactor and was subjected to filtration to remove the catalyst and the inorganic salt. Then the solvent was recovered from the filtrate to provide 3.1 g (88.3%) of a viscous product. The hydrochloride of the product showed a melting point of 177° to 178° C. which was the same as that of the compound prepared by the conventional process.

EXAMPLE 22

Synthesis of β-piperidinoethyl 3-methylflavone-8-carboxylate

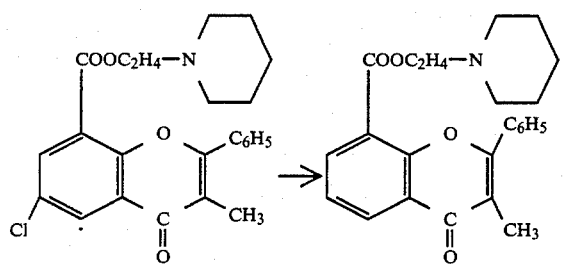

Into a pressure reactor were placed 4.13 g (0.01 mole) of β-piperidinoethyl 6-chloro-3-methylflavone-8-carboxylate, 4.0 g (0.03 mole) of sodium acetate, 150 ml of isopropanol and 0.2 g of 5% palladium-carbon catalyst. After the atmosphere was replaced with hydrogen gas, reaction was conducted at a pressure of 5.0 kg/cm$^2$G at 70° C. for 6 hours. After completion of the reaction, the contents of the reactor were withdrawn and filtered to remove the catalyst and the inorganic salt while being hot. Then the solvent was recovered and the residue was washed with water and dried to give 3.8 g (96.2%) of white crystals melting at 83° to 85° C. which were recrystallized from alcohol to obtain 3.2 g (81.8%) of β-piperidinoethyl 3-methylflavone-8-carboxylate melting at 85° to 86° C. The product was treated with a hydrochloric acid-alcohol mixture to afford the hydrochloride of the product melting at 232° to 234° C. which was identical in melting point with β-piperidinoethyl 3-methylflavone-8-carboxylate hydrochloride prepared by the conventional method. These two compounds, when melted together, showed a melting point not lower than that of each compound.

EXAMPLE 23

Synthesis of morpholinoethyl 3-methylflavone-8-carboxylate

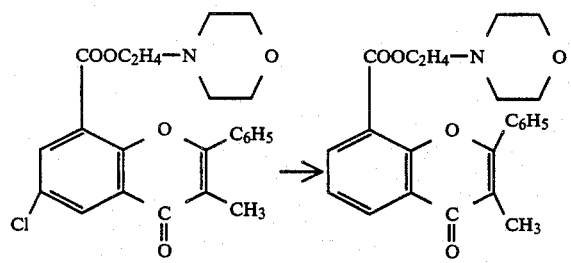

Into a pressure reactor were placed 4.3 g (0.01 mole) of morpholinoethyl 6-chloro-3-methylflavone-8-carboxylate, 4.0 g (0.03 mole) of sodium acetate, 150 ml of isopropanol and 0.2 g of 5% palladium-carbon catalyst. After the atmosphere was replaced with hydrogen gas, reaction was carried out at a pressure of 5.0 kg/cm$^2$G at 70° C. for 6 hours. Thereafter the contents were withdrawn from the reactor and were subjected to filtration to remove the catalyst and the inorganic salt, etc. while being hot. The same subsequent procedure as in Example 15 was followed to provide 3.7 g (94.5%) of a salt of morpholinoethyl 3-methylflavone-8-carboxylate. The salt was treated with a hydrochloric acid-alcohol mixture and was recrystallized from alcohol to give white crystals of morpholinoethyl 3-methylflavone-8-carboxylate hydrochloride melting at 233° to 234° C. The product thus obtained was identical in melting point with morpholinoethyl 3-methylflavone-8-carboxylate hydrochloride prepared by the conventional method. These two compounds were melted together and was found to have a melting point which was not lower than that of the individual compounds.

EXAMPLE 24

Synthesis of 3-methylflavone-8-carboxylic acid

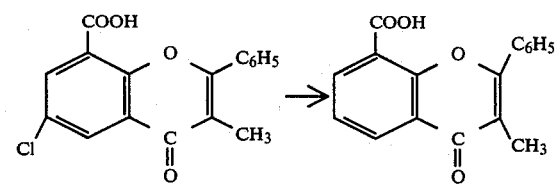

Into a pressure reactor were placed 3.15 g (0.01 mole) of 6-chloro-3-methylflavone-8-carboxylic acid, 4.0 g (0.03 mole) of sodium acetate, 150 ml of isopropanol and 0.2 g of 5% palladium-carbon catalyst. After the atmosphere was replaced with hydrogen gas, reaction was performed at a pressure of 5.0 kg/cm$^2$G at 70° C. for 6 hours. Then the reaction mixture was treated in the same manner as in Example 13, affording 2.6 g (93%) of 3-methylflavone-8-carboxylic acid which was recrystallized from alcohol, giving a product melting at 230° to 233° C.

The product thus obtained was identical in melting point with 3-methylflavone-8-carboxylic acid prepared by the conventional method. When melted together, these two compounds exhibited a melting point not lower than that of each compound.

EXAMPLE 25

Synthesis of methyl 3-methylflavone-8-carboxylate

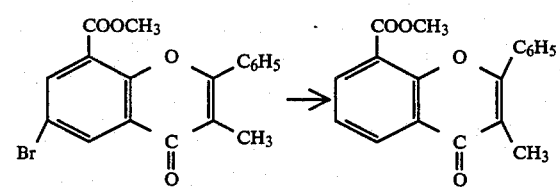

The procedure of Example 20 was repeated with the exception of using 1.7 g (4.57 m mole) of methyl 6-bromo-3-methylflavone-8-carboxylate in place of methyl 6-chloro-3-methylflavone-8-carboxylate, giving 1.2 g (89.3%) of white needle-like crystals melting at 162.6° to 166.5° C. which were recrystallized from alcohol to provide a product melting at 166.4° to 168.4° C.

EXAMPLE 26

Synthesis of β-piperidinoethyl 3-methylflavone-8-carboxylate

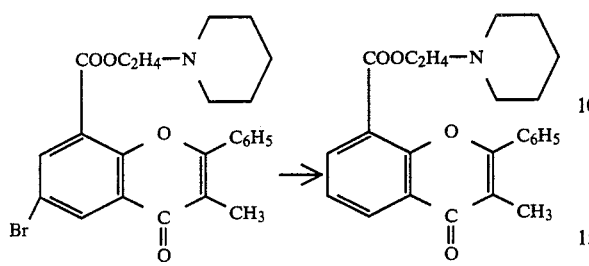

The procedure of Example 22 was repeated with the exception of using 4.7 g (0.01 mole) of β-piperidinoethyl 6-bromo-3-methylflavone-8-carboxylate in place of β-piperidinoethyl 6-chloro-3-methylflavone-8-carboxylate, giving 3.8 g (97.1%) of crystals melting at 82.0° to 85.0° C. which were recrystallized from alcohol to provide 3.2 g (81.1%) of white crystals melting at 84.5° to 86.0° C.

EXAMPLE 27

Synthesis of β-piperidinoethyl 3-methylflavone-8-carboxylate (hydrochloride)

(a)

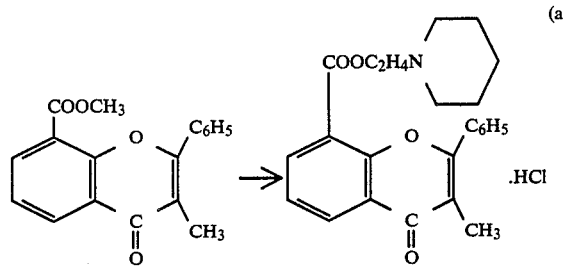

(1) A 29.4 g (0.10 mole) quantity of methyl 3-methylflavone-8-carboxylate was added to 200 ml of a solution of 0.5N—KOH in methanol. The mixture was refluxed with heating for 3 hours and the solvent was removed by distillation. To the residue was added 300 ml of water to dissolve the residue in water and the solution was subjected to filtration. The filtrate was neutralized with dilute hydrochloric acid to give 27.3 g (97.5%) of 3-methylflavone-8-carboxylic acid, M.P. 229° to 231.5° C.

(2) To 14.0 g (0.05 mole) of 3-methyl-flavone-8-carboxylic acid were added 14.9 g (0.125 mole) of thionyl chloride and 100 ml of anhydrous benzene. The mixture was refluxed with heating for 5 hours, and the solvent and the excess thionyl chloride were distilled off to obtain 14.9 g of solids.

(3) To the product obtained above in (2) were added 7.0 g (0.054 mole) of piperidinoethanol and 100 ml of anhydrous benzene. The mixture was refluxed with heating for 3 hours and white crystals formed were filtered off, washed with benzene and dried, giving 21.0 g of a product in a yield of 98.2% (based on 3-methylflavone-8-carboxylic acid), M.P. 211° to 232° C.

(4) The product obtained above was recrystallized from alcohol to give 17.2 g (80.5%) melting at 232.0° to 233.2° C. of white needle-like crystals.

(b)

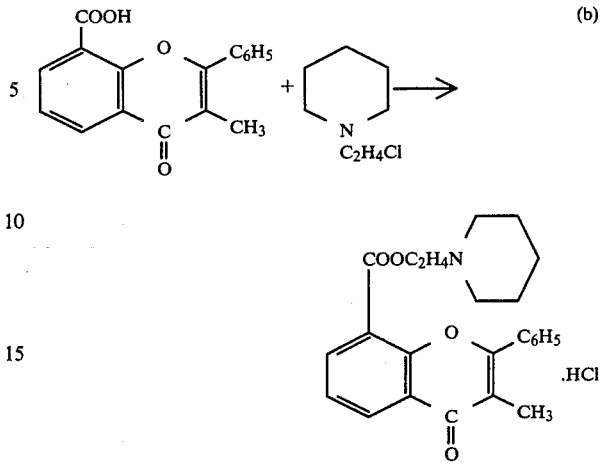

To 100 ml of anhydrous benzene was added 14.0 g (0.05 mole) of 3-methylflavone-8-carboxylic acid to obtain a suspension. To the suspension was added 8.0 g (0.054 mole) of piperidinoethyl chloride. The mixture was refluxed with heating for 5 hours. The separated white crystals were filtered off, washed with benzene and dried to provide 20.9 g (97.8%) of white crystals melting at 209° to 229° C.

The crystals thus formed were recrystallized from alcohol to obtain 17.5 g (81.9%) of white crystals melting at 231.8° to 233.0° C.

(c)

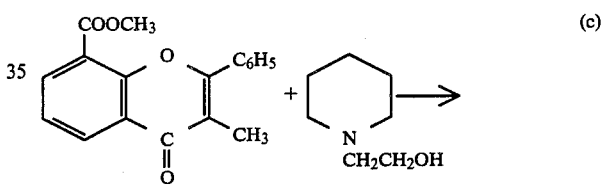

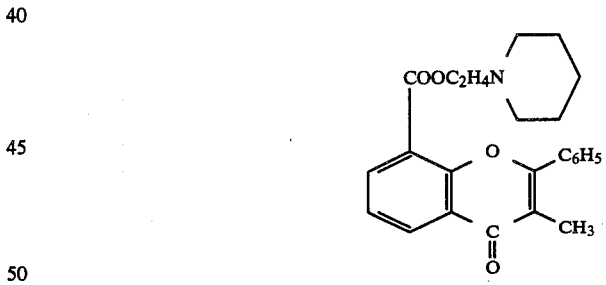

A 29.4 g (0.10 mole) quantity of methyl 3-methylflavone-8-carboxylate was added to a solution of 0.5 g (0.022 mole) of sodium in 300 ml of piperidinoethanol. The mixture was maintained at room temperature for 24 hours and heated at 90° C. for 2 hours. The reaction mixture was subjected to distillation to remove the excess piperidinoethanol and the methanol produced. The residue was dissolved in dilute hydrochloric acid, purified and neutralized with sodium carbonate to provide a crude product.

The product was obtained in an amount of 36.3 g (92.8%) with a melting point of 82.0° to 84.8° C. and was recrystallized from alcohol to afford 34.8 g (89% yield) of crystals melting at 84.5° to 86.0° C. The hydrochloride of the product was found to have a melting point of 232° to 234° C.

We claim:

1. A derivative of 3-methylflavone-8-carboxylic acid represented by the formula (I)

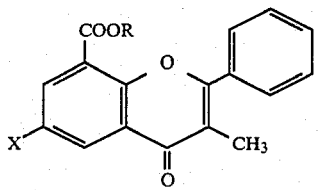
(I)

wherein R represents a hydrogen atom, a lower alkyl group or a group

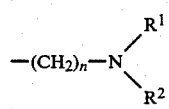

(wherein $R^1$ and $R^2$ represent a lower alkyl group or $R^1$ and $R^2$, when taken together with the nitrogen atom to which they are attached, may form a heterocyclic ring with or without an intervening hetero atom, and n is an integer of 1 to 4), and X represents a halogen atom.

2. A compound as defined in claim 1 wherein R is a hydrogen atom.

3. A compound as defined in claim 1 wherein R is a lower alkyl group.

4. A compound as defined in claim 3 wherein the lower alkyl group is methyl or ethyl.

5. A compound as defined in claim 1 wherein R is a group

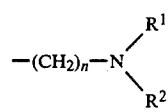

(wherein $R^1$, $R^2$ and n are as defined in claim 1).

6. A compound as defined in claim 5 wherein $R^1$ and $R^2$ are lower alkyl groups.

7. A compound as defined in claim 6 wherein the lower alkyl group is methyl.

8. A compound as defined in claim 5 wherein the group

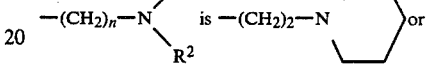

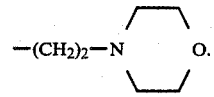

9. A compound as defined in claim 1 wherein X is chlorine.

10. A compound as defined in claim 1 wherein X is bromine.

* * * * *